United States Patent
Matsui et al.

(10) Patent No.: US 6,365,745 B1
(45) Date of Patent: Apr. 2, 2002

(54) METHOD FOR PRODUCING HYDRAZINE DERIVATIVE

(75) Inventors: Kozo Matsui; Kiyoshi Sugi, both of Osaka; Hiromi Suga, Chiryu; Nobushige Itaya, Osaka, all of (JP)

(73) Assignee: Sumika Fine Chemicals Co., Ltd., Osaka (JP)

( * ) Notice: Subject to any disclaimer, the term of this patent is extended or adjusted under 35 U.S.C. 154(b) by 0 days.

(21) Appl. No.: 09/905,442

(22) Filed: Jul. 13, 2001

(30) Foreign Application Priority Data

Jul. 14, 2000 (JP) .......................... 12-215031

(51) Int. Cl.⁷ ................... C07D 213/04; C07C 241/02
(52) U.S. Cl. .................. 546/332; 564/148; 564/149; 564/151; 560/34
(58) Field of Search .................. 546/332; 560/34; 564/148, 149, 151

(56) References Cited

FOREIGN PATENT DOCUMENTS

| WO | WO 97/40029 | 10/1997 |
|---|---|---|
| WO | WO 01/27083 | 4/2001 |

*Primary Examiner*—Charanjit S. Aulakh
(74) *Attorney, Agent, or Firm*—Leydig, Voit & Mayer, Ltd.

(57) ABSTRACT

The present invention provides a method for producing a hydrazine derivative of the formula [2]:

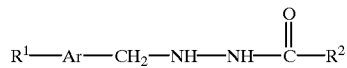

[2]

wherein $R^1$ is alkyl group having 1–12 carbon atoms and the like, $R^2$ is alkyl group having 1–12 carbon atoms and the like, and Ar is phenylene group and the like, from a hydrazone derivative of the formula [1]

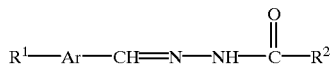

[1]

wherein $R^1$, $R^2$ and Ar are as defined above, in the presence of at least one base selected from the group consisting of an organic base and an inorganic base, and a metal hydrogenating catalyst. By this method, reduction proceeds selectively and a hydrogenolysis reaction (side reaction) can be suppressed.

10 Claims, No Drawings

METHOD FOR PRODUCING HYDRAZINE DERIVATIVE

TECHNICAL FIELD OF THE INVENTION

The present invention relates to a method for producing a specific hydrazine derivative useful as a starting material for pharmaceutical products.

BACKGROUND OF THE INVENTION

A hydrazine derivative useful as a starting material for pharmaceutical products, such as tert-butyl 3-[4-(pyridin-2-yl)benzyl]carbazate of the following formula [3] is useful as an intermediate for the anti-AIDS agent described in WO97/40029

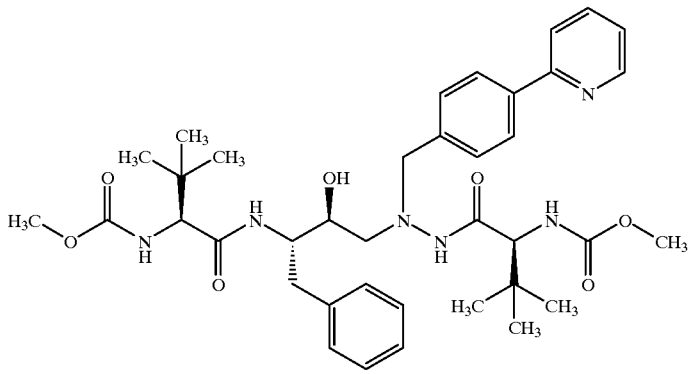

and this intermediate is known to be obtained by reducing N-(tert-butoxycarbonyl)-N'-{[4-(pyridin-2-yl)phenyl]methylidene}hydrazone of the following formula [4] in methanol in the presence of 10% Pd/C (WO97/40029, Example 46C). However, there is no detailed explanation or reference to the by-product and the like caused by the reduction.

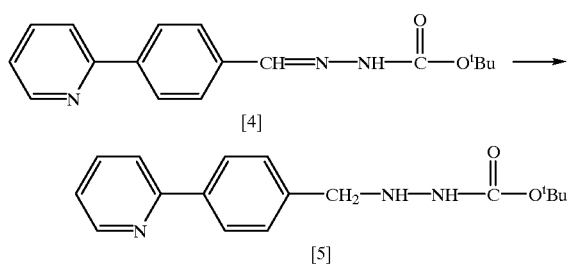

The present inventors have reduced hydrazone [4] according to Example 46C of WO97/40029 and noted the formation of 4-(pyridin-2-yl)toluene as a by-product resulting from hydrogenolysis of the compound of the formula [3]. They have confirmed that the formation of the by-product lowers the selectivity toward the compound of the formula [3] and that the by-product behaves as a contaminant in the solution and prevents high yield crystallization of the compound of the formula [3]. In view of this, a method for the production of a hydrazine derivative of the formula [3] from a hydrazone derivative of the formula [4] is demanded, by which method the reduction proceeds selectively and a hydrogenolysis reaction (side reaction) can be suppressed.

It is therefore an object of the present invention to provide a method for producing a hydrazine derivative from a hydrazone derivative. According to this method, the reduction proceeds selectively and a hydrogenolysis reaction (side reaction) can be suppressed.

SUMMARY OF THE INVENTION

According to the present invention, there has now been found that the objective reduction proceeds selectively and hydrogenolysis reaction (side reaction) is suppressed by adding, together with a metal hydrogenating catalyst, at least one base selected from the group consisting of an organic base and an inorganic base to the reaction system when producing a hydrazine derivative of the following formula [2] from a hydrazone derivative of the following formula [1].

That is, the present invention relates to a method for producing a hydrazine derivative of the formula [2]:

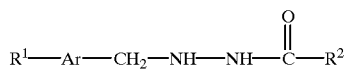

[2]

wherein
R$^1$ is alkyl group having 1–12 carbon atoms, alkoxy group having 1–6 carbon atoms, halogen atom, hydroxyl group, optionally substituted phenyl group, optionally substituted aralkyl group or optionally substituted aromatic heterocyclic group,
R$^2$ is alkyl group having 1–12 carbon atoms, alkoxy group having 1–6 carbon atoms, halogen atom, optionally substituted phenyl group, optionally substituted aralkyl group, optionally substituted phenylalkoxy group or optionally substituted aromatic heterocyclic group, and
Ar is phenylene group, naphthylene group or aromatic heterocyclic group (hereinafter to be referred to as hydrazine compound [2]),
which method comprises reducing a hydrazone derivative of the formula [1]

[1]

wherein R$^1$, R$^2$ and Ar are as defined above (hereinafter to be referred to as hydrazone compound [1]), in the presence of at least one base selected from the group consisting of an organic base and an inorganic base, and a metal hydrogenating catalyst.

The organic base is preferably a tertiary amine, more preferably triethylamine, and the inorganic base is preferably an alkali metal carbonate, more preferably sodium carbonate. After the reduction reaction, the reaction mixture is cooled as necessary, and filtrated in an atmosphere of an inert gas alone (e.g., nitrogen gas and the like), hydrogen gas alone or a mixed gas of these, whereby the reverse reaction (oxidation reaction) to the hydrazone compound [1] can be suppressed and the hydrazine compound [2] can be obtained in a high yield. For example, after the reduction reaction, the reaction mixture is cooled to not higher than 30° C., and filtrated in an atmosphere of inert gas alone. After the reduction reaction, moreover, a sulfur compound (preferably sodium hydrosulfite) is added to the filtrate obtained by the filtration of the reaction mixture to give a stable hydrazine compound [2] even in a solution state.

DETAILED DESCRIPTION OF THE INVENTION

The present invention is explained in detail in the following.

The "alkyl group having 1–12 carbon atoms" at $R^1$ and $R^2$ is a linear or branched chain, and is, for example, methyl, ethyl, propyl, isopropyl, butyl, isobutyl, sec-butyl, tert-butyl, pentyl, hexyl, heptyl, octyl, nonyl, decyl, undecyl, dodecyl and the like, preferably alkyl group having 1–6 carbon atoms.

The "alkoxy group having 1–6 carbon atoms" at $R^1$ and $R^2$ is a linear or branched chain, and is, for example, methoxy, ethoxy, propoxy, isopropoxy, butoxy, isobutoxy, sec-butoxy, tert-butoxy, pentyloxy, hexyloxy and the like, preferably alkoxy group having 1–4 carbon atoms.

The "halogen atom" at $R^1$ and $R^2$ is chlorine atom, fluorine atom, bromine atom or iodine atom, which is preferably chlorine atom, fluorine atom or bromine atom.

The substituent of "optionally substituted phenyl group" at $R^1$ and $R^2$ is not subject to any particular limitation as long as it does not reduce under the reduction conditions employed in the present invention, and is exemplified by alkyl group having 1–12 carbon atoms (linear or branched chain such as methyl, ethyl, propyl, isopropyl, butyl, sec-butyl, tert-butyl, pentyl, hexyl, heptyl, octyl, nonyl, decyl, undecyl, dodecyl and the like), alkoxy group having 1–6 carbon atoms (linear or branched chain such as methoxy, ethoxy, propoxy, isopropoxy, butoxy, isobutoxy, sec-butoxy, tert-butoxy, pentyloxy, hexyloxy and the like), halogen atom (fluorine atom, bromine atom, iodine atom, chlorine atom) and the like. Phenyl group may be substituted with one or more of these substituents.

The aralkyl group of "optionally substituted aralkyl group" at $R^1$ and $R^2$ is that wherein the aryl moiety is phenyl, naphthyl etc., and the alkyl moiety is alkyl group having 1 to 4, preferably 1 or 2, carbon atoms, and is exemplified by benzyl, 1-phenylethyl, 2-phenylethyl and the like. The substituent is not subject to any particular limitation as long as it does not reduce under the reduction conditions employed in the present invention, and is exemplified by alkyl group having 1–12 carbon atoms (linear or branched chain such as methyl, ethyl, propyl, isopropyl, butyl, sec-butyl, tert-butyl, pentyl, hexyl, heptyl, octyl, nonyl, decyl, undecyl, dodecyl and the like), alkoxy group having 1–6 carbon atoms (linear or branched chain, such as methoxy, ethoxy, propoxy, isopropoxy, butoxy, isobutoxy, sec-butoxy, tert-butoxy, pentyloxy, hexyloxy and the like), halogen atom (fluorine atom, bromine atom, iodine atom, chlorine atom) and the like. It may be substituted with one or more of these substituents.

The aromatic heterocyclic group of "optionally-substituted aromatic heterocyclic group" at $R^1$ and $R^2$ is exemplified by pyridyl, pyrimidinyl, pyridazinyl, pyrazinyl, imdazolyl, pyrazolyl, oxazolyl, isoxazolyl, thienyl, furyl, indolyl and the like, preferably pyridyl. The substituent is not subject to any particular limitation as long as it does not reduce under the reduction conditions employed in the present invention, and is exemplified by alkyl group having 1–12 carbon atoms (linear or branched chain such as methyl, ethyl, propyl, isopropyl, butyl, sec-butyl, tert-butyl, pentyl, hexyl, heptyl, octyl, nonyl, decyl, undecyl, dodecyl and the like), alkoxy group having 1–6 carbon atoms (linear or branched chain, such as methoxy, ethoxy, propoxy, isopropoxy, butoxy, isobutoxy, sec-butoxy, tert-butoxy, pentyloxy, hexyloxy and the like), halogen atom (fluorine atom, bromine atom, iodine atom, chlorine atom) and the like.

It may be substituted with one or more of these substituents.

The alkoxy group of "phenylalkoxy group optionally having a substituent(s)" at $R^2$ is preferably linear or branched chain alkoxy group having 1–6 carbon atoms, and is exemplified by methoxy, ethoxy, propoxy, isopropoxy, butoxy, isobutoxy, sec-butoxy, tert-butoxy, pentyloxy, hexyloxy and the like. The alkoxy group may be substituted by any substituents as long as it does not reduce under the reduction conditions employed in the present invention. It may be substituted with one or more of these substituents.

The "aromatic heterocyclic group" at Ar is a divalent aromatic heterocyclic group. The aromatic heterocycle is exemplified by pyridine, pyrimidine, pyridazine, pyrazine, imidazole, pyrazole, oxazole, isoxazole, thiophene, furan, indole and the like, preferably pyridine.

In the present invention, hydrazine compound [2] can be obtained by reducing the hydrazone compound [1] in the presence of at least one base selected from the group consisting of an organic base and an inorganic base, and a metal hydrogenating catalyst. To be specific, hydrazone compound [1], a metal hydrogenating catalyst and a base are added to a solvent, and the mixture is stirred under an atmosphere of hydrogen gas.

The solvent to be used for the reduction in the present invention is any as long as it dissolves hydrazone compound [1] and exerts no adverse influence on the reaction. Examples thereof include alcohol solvents (e.g., methanol, isopropanol and the like), ester solvents (e.g., ethyl acetate and the like), ether solvents (e.g., tetrahydrofuran (THF), ether and the like), hydrocarbon solvents (e.g., toluene and the like), and a mixed solvent of these, with preference given to methanol and isopropanol. These solvents may contain a small amount of water. The amount of use of the solvent is preferably about from 4-fold weight to 5-fold weight relative to the hydrazone compound [1].

The metal hydrogenating catalyst to be used for the reduction in the present invention is a metal catalyst generally used as a hydrogenating catalyst. Examples of the metal catalyst include palladium catalysts, platinum catalysts and nickel catalysts. Of these metal hydrogenating catalysts, palladium catalysts are preferable and Pd/C is most preferable. The amount of use of the catalyst varies depending on the kind of the catalyst to be used. When 5% Pd/C is used, for example, the amount of use of the 5% Pd/C is preferably from 0.5 part by weight to 5 parts by weight, more preferably from 1 part by weight to 3 parts by weight, per 100 parts by weight of the hydrazone compound [1].

In the reduction reaction of the present invention, the presence of at least one base selected from the group consisting of an organic base and an inorganic base can suppress hydrogenolysis, which is a side reaction. As the organic base, amines, tertiary amines (e.g., triethylamine and the like) are preferable, and triethylamine is particularly preferable from the economical aspect. As the inorganic base, alkali metal carbonate is preferable, and potassium carbonate and sodium carbonate are more preferable from the economical aspect. These may be mixed before use, wherein triethylamine and sodium carbonate are preferably combined.

When one of the organic base and inorganic base is used, the base is preferably used in an amount of 0.01 mol–0.5 mol per 1 mol of the hydrazone compound [1]. When, for example, two or more kinds of organic bases (or inorganic bases) are used in this case, the total amount of use of the bases should fall within the above range. When an organic base and an inorganic base are mixed for use, the organic base is preferably used in an amount of 0.01 mol–0.5 mol, and the inorganic base is preferably used in an amount of 0.005 mol–0.1 mol, per 1 mol of the hydrazone compound [1].

The amount of hydrogen used for the reduction in the present invention may be any as long as it can reduce the hydrazone compound [1], and it may be introduced into the reaction system until the absorption of hydrogen stops. The hydrogen is used at a pressure of preferably from atmospheric pressure to 10 atm, more preferably from atmospheric pressure to 5 atm.

The temperature of reduction in the present invention varies depending on the solvent to be used and the like. For example, reduction is carried out in an alcohol solvent at a temperature of generally from 40° C. to 80° C., preferably from 40° C. to 60° C., more preferably from 40° C. to 50° C., wherein the termination of hydrogen absorption is the end point of the reaction. The reaction generally ends in 2 hours to 12 hours, preferably 5 hours to 8 hours.

The present inventors have found that a reverse reaction (oxidation reaction) to hydrazone compound [1] (the starting material) can be suppressed by filtration after reduction, under the atmosphere for reduction (i.e., atmosphere containing hydrogen gas); by filtration of the reaction mixture after reduction, under an atmosphere of hydrogen gas alone or a mixed gas of hydrogen gas and an inert gas, or by cooling the reaction mixture and filtration under an atmosphere of inert gas alone after reduction. For example, when the reaction mixture is cooled after reduction and filtrated at the same temperature under an atmosphere of an inert gas alone (i.e., under atmosphere free of hydrogen gas), the cooling temperature is generally not higher than 30° C., preferably not higher than 10° C. When it exceeds 30° C., a reverse reaction tends to proceed easily and the yield of hydrazine compound [2] decreases. The reaction mixture is preferably filtrated in a mixed gas of an inert gas and hydrogen gas, where a filtration temperature is not particularly limited.

The hydrazine compound [2] obtained by reducing, filtrating the reaction mixture, adding a sulfur compound to the resultant filtrate and isolating the compound is stable even in a solution state. This is considered to be attributable to the fact that the addition of the sulfur compound inactivates the metal hydrogenating catalyst remaining in the reaction mixture.

The sulfur compound to be used in the present invention may be a simple substance of sulfur, carbon disulfide, a derivative having an —SH group, a derivative potentially having an —SH group or a derivative having an S—S bond, preferably a derivative potentially having an —SH group.

The derivative having an —SH group has one or more —SH groups. Examples thereof include hydrogen sulfide, salt of thiol (e.g., NaSH, NH$_4$SH, KSH and the like), alkanethiol (e.g., methanethiol, ethanethiol, propanethiol and the like), arenethiol (e.g., benzenethiol and the like) and derivatives having two or more —SH groups (e.g., ethanedithiol and the like).

The derivative potentially having an —SH group is a derivative that originally does not have an —SH group but comes to have one by neutralization or substitution of the counter ion with hydrogen atom. Examples thereof include a derivative having an —SNa group, since —SNa group becomes —SH group by neutralization. Specific examples thereof include sodium sulfide, ammonium sulfide and sodium hydrosulfite, preferably sodium hydrosulfite.

The derivative having an S—S bond has one or more S—S bonds. Examples thereof include organic disulfide derivative (e.g., dimethyl disulfide, diphenyl disulfide and the like), organic polysulfide derivative having 3 or more sequential S—S bonds and inorganic polysulfide derivative (e.g., ammonium polysulfide and the like).

The amount of the sulfur compound varies depending on the kind of sulfur compound, and the kind and amount of the metal hydrogenating catalyst present in the filtrate, and the sulfur compound can be added until the catalyst present in the filtrate is inactivated. For example, when palladium-carbon is used as a metal hydrogenating catalyst in an amount of 5 wt % of part by weight of hydrazone derivative (I), sodium hydrosulfite is used as a sulfur compound, and a filtrate obtained is added directly into a container containing a sulfur compound, the sulfur compound is used in an amount of 1–10 wt %, preferably 3–6 wt %, of part by weight of hydrazone derivative (I).

The sulfur compound may be added at generally 10–60° C., preferably 20–40° C. The time until the completion of the inactivation of the metal hydrogenating catalyst varies depending on the amount of use and the like of the metal hydrogenating catalyst. The metal hydrogenating catalyst is generally inactivated in 10 min–60 min.

The hydrazine compound [2] can be isolated and purified by a conventional method.

The hydrazone compound [1], which is a starting material, can be produced by a known method, such as the following two methods.

(i) According to the following scheme, an aldehyde compound 1 is reacted with hydrazine to give a hydrazone compound 2, and, using a base as an acid scavenger, the compound 2 is reacted with an acylating agent.

(ii) Alternatively, according to the following scheme, an aldehyde compound 1 and an acyl-hydrazine compound 3 are reacted.

$$R^1\text{—Ar—}\overset{\overset{O}{\|}}{C}H \xrightarrow{NH_2NH_2}$$
1

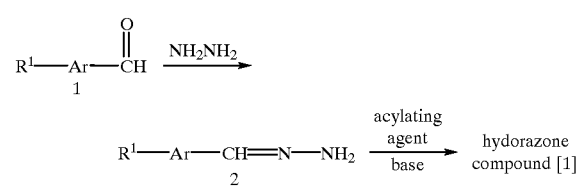

-continued

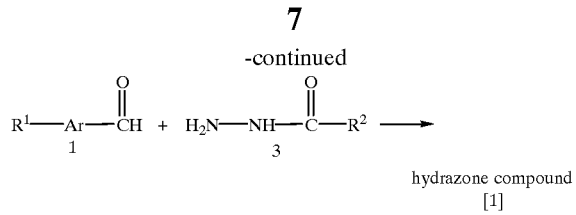

hydrazone compound [1]

The hydrazine compound [2] obtained according to the method of the present invention can be converted to a pharmaceutical product compound by a method described in WO97/40029.

The present invention is explained in detail by referring to Reference Examples, Comparative Examples and Examples. The present invention is not limited by these examples in any way. In the following Tables [I]–[III] respectively correspond to the following compounds [I]–[III].

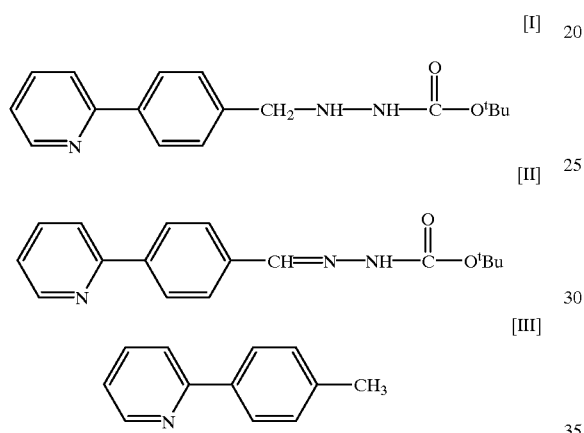

Reference Example 1

Reduction Without Addition of Base

N-(tert-Butoxycarbonyl)-N'-{[4-(pyridin-2 yl)phenyl]methylidene}hydrazine (5 g, 16.82 mmol) and 5% Pd/C [0.125 g, 2.5 wt % of N-(tert-butoxycarbonyl)-N'-{[4-(pyridin-2yl)phenyl]methylidene}hydrazine] were added to methanol (25 ml). After displacement with hydrogen, the mixture was reduced at atmospheric pressure and at 50° C. for 5 h. After the reaction, a part of the reaction mixture was taken and analyzed by high performance liquid chromatography (HPLC). As a result, the composition was found to contain N-(tert-butoxycarbonyl)-N'-[4-(pyridin-2-yl)benzyl]hydrazine corresponding to 97.11%, 4-(pyridin-2-yl)toluene corresponding to 2.69%, N-(tert-butoxycarbonyl)-N'-{[4-(pyridin-2yl)phenyl]methylidene}hydrazine (starting material) corresponding to 0.36%.

Examples 1–3

Reduction With the Addition of Base

In the same manner as in Reference Example 1 except that the reaction conditions shown in Table 1 were employed, the reaction was carried out. The base was added in addition to a metal hydrogenating catalyst before hydrogen gas was introduced. The obtained reaction mixture was analyzed by HPLC and the results are as shown in Table 1. The amount of use of base in Table 1 is in the number of moles relative to 1 mol of the compound of formula [II] (starting material).

TABLE 1

| | Reaction conditions | | | | Production ratio (mol %) | | |
|---|---|---|---|---|---|---|---|
| | Temp. (° C.) | Time (h) | Hydrogen pressure | Base (amount used) | Objective product [I] | Starting material [II] | Hydrogenolysate [III] |
| Ref. Ex. 1 | 50 | 5 | Atm. pressure | none | 97.11 | 2.69 | 0.36 |
| Ex. 1 | 40 | 5 | Atm. pressure | Triethylamine (0.1 mol) | 99.17 | 0 | 0.69 |
| Ex. 2 | 40 | 5 | Atm. pressure | sodium carbonate (0.047 mol) | 99.16 | 0.16 | 0.25 |
| Ex. 3 | 40 | 8 | Atm. pressure | Triethylamine (0.05 mol) sodium carbonate (0.009 mol) | 99.76 | 0.06 | 0 |

Comparative Example 1 and Example 4

The reaction mixture obtained in the same manner as in Reference Example 1 above was stirred in a nitrogen gas under the conditions shown in Table 2 and analyzed by HPLC. The results are as shown in Table 2.

Comparative Example 2 AND Example 5

The reaction mixture obtained in the same manner as in Example 1 above was stirred in a nitrogen gas under the conditions shown in Table 2 and analyzed by HPLC. The results are as shown in Table 2.

Example 6 and 7

The reaction mixture obtained in the same manner as in Reference Example 1 above was stirred in a hydrogen/nitrogen (1/2) mixed gas under the conditions shown in Table 2 and analyzed by HPLC. The results are as shown in Table 2.

TABLE 2

| | Stirring conditions | | | Production ratio (mol %) | | |
|---|---|---|---|---|---|---|
| | | | | Objective product [I] before stirring/after stirring | Starting material [II] before stirring/after stirring | Hydrogenolysate [III] before stirring/after stirring |
| | Temp. (° C.) | Time (h) | Kind of gas (atm) | | | |
| Comp. Ex. 1 | 57–58 | 5 | nitrogen (2 atm) | 97.67/ 97.16 | 0.11/ 0.33 | 2.11/ 2.38 |
| Comp. Ex. 2 | 57–58 | 5 | nitrogen (2 atm) | 99.76/ 99.14 | 0.06/ 0.19 | 0/0 |

TABLE 2-continued

| | Stirring conditions | | | Production ratio (mol %) | | |
|---|---|---|---|---|---|---|
| | Temp. (° C.) | Time (h) | Kind of gas (atm) | Objective product [I] before stirring/after stirring | Starting material [II] before stirring/after stirring | Hydrogen-olysate [III] before stirring/after stirring |
| Ex. 4 | 5–10 | 8 | nitrogen (2 atm) | 94.41/ 94.85 | 0.10/ 0.10 | 4.71/ 4.68 |
| Ex. 5 | 5–10 | 8 | nitrogen (2 atm) | 99.76/ 99.77 | 0.06/ 0.06 | 0/0 |
| Ex. 6 | 40–42 | 5 | hydrogen/ nitrogen (1/2) (2 atm) | 99.35/ 99.35 | 0.06/ 0.02 | 0.59/ 0.63 |
| Ex. 7 | 58–62 | 5 | hydrogen/ nitrogen (1/2) (2 atm) | 97.63/ 97.20 | 0.09/ 0.04 | 0.10/ 0.21 |

According to the present invention, the objective reduction proceeds selectively and a hydrogenolysis reaction (side reaction) is suppressed when producing hydrazine compound [2] from hydrazone compound [1].

In this way, the objective compound can be obtained in a high yield.

Example 8

The reaction mixture of Example 3 was filtrated in a hydrogen/nitrogen (ca. 1/2) mixed gas and sodium hydrosulfite (100 mg) was added to the obtained filtrate at the same temperature, which was followed by evaporation of methanol under reduced pressure. To the obtained residue was added heptane/isopropanol (volume ratio=9/1). The mixture was heated to 65° C. and filtrated in a nitrogen gas, after which the filtrate was cooled to allow crystallization to give N-(tert-butoxycarbonyl)-N'-[4-(pyridin-2-yl)benzyl] hydrazine (4.2 g, yield: 83%). As a result of the HPLC analysis of the crystals, a peak corresponding to the starting material, N-(tert-butoxycarbonyl)-N'-{[4-(pyridin-2-yl) phenyl]methylidene}-hydrazine, was not detected.

This application is based on patent application No. 215031/2000 filed in Japan, the contents of which are hereby incorporated by reference.

What is claimed is:

1. A method for producing a hydrazine derivative of the formula [2]:

wherein
R$^1$ is alkyl group having 1–12 carbon atoms, alkoxy group having 1–6 carbon atoms, halogen atom, hydroxyl group, optionally substituted phenyl group, optionally substituted aralkyl group or optionally substituted aromatic heterocyclic group,
R$^2$ is alkyl group having 1–12 carbon atoms, alkoxy group having 1–6 carbon atoms, halogen atom, optionally substituted phenyl group, optionally substituted aralkyl group, optionally substituted phenylalkoxy group or optionally substituted aromatic heterocyclic group, and
Ar is phenylene group, naphthylene group or aromatic heterocyclic group,
which method comprises reducing a hydrazone derivative of the formula [1]

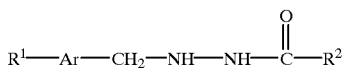

wherein R$^1$, R$^2$ and Ar are as defined above, in the presence of at least one base selected from the group consisting of an organic base and an inorganic base, and a metal hydrogenating catalyst.

2. The method of claim 1, wherein the organic base is a tertiary amine.

3. The method of claim 2, wherein the tertiary amine is triethylamine.

4. The method of claim 1, wherein the inorganic base is alkali metal carbonate.

5. The method of claim 4, wherein the alkali metal carbonate is sodium carbonate.

6. The method of claim 1, which further comprises, after reduction, filtrating an obtained reaction mixture under an atmosphere of hydrogen gas alone or a mixed gas of hydrogen gas and an inert gas.

7. The method of claim 1, which further comprises, after reduction, cooling an obtained reaction mixture and filtrating the mixture under an atmosphere of an inert gas alone.

8. The method of claim 7, wherein the cooling temperature is not more than 30° C.

9. The method of claim 1, which further comprises, after reduction, adding a sulfur compound to a filtrate obtained after filtration of the reaction mixture.

10. The method of claim 9, wherein the sulfur compound is sodium hydrosulfite.

* * * * *

UNITED STATES PATENT AND TRADEMARK OFFICE
CERTIFICATE OF CORRECTION

PATENT NO.   : 6,365,745 B1
DATED        : April 2, 2002
INVENTOR(S)  : Matsui et al.

It is certified that error appears in the above-identified patent and that said Letters Patent is hereby corrected as shown below:

Column 1,
Lines 41-52:

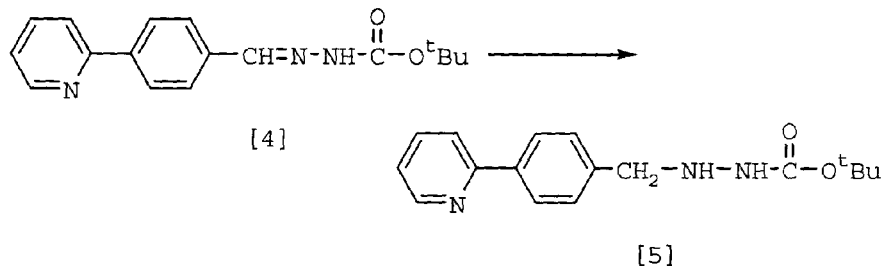

should read

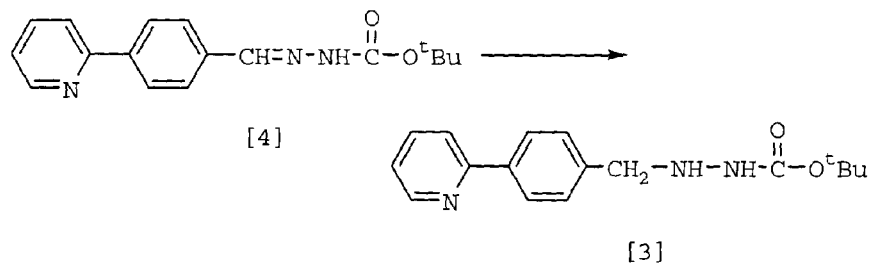

Signed and Sealed this

Fourteenth Day of January, 2003

JAMES E. ROGAN
*Director of the United States Patent and Trademark Office*